United States Patent [19]

Sheng et al.

[11] B 3,983,143

[45] Sept. 28, 1976

[54] EPOXIDATION OF OLEFINS WITH LESS STABLE ORGANIC HYDROPEROXIDES BY USING AN ALCOHOL STABILIZING AGENT

[75] Inventors: Ming N. Sheng, Cherry Hill, N.J.; John G. Zajacek, Devon, Pa.; Thomas N. Baker, III, Sudbury, Mass.

[73] Assignee: Atlantic Richfield Company, Los Angeles, Calif.

[22] Filed: Nov. 6, 1974

[21] Appl. No.: 521,324

[44] Published under the second Trial Voluntary Protest Program on January 27, 1976 as document No. B 521,324.

Related U.S. Application Data

[60] Division of Ser. No. 290,592, Sept. 20, 1972, Pat. No. 3,862,961, which is a continuation-in-part of Ser. No. 95,375, Dec. 4, 1970, abandoned.

[52] U.S. Cl. .................. 260/348.5 L; 252/431 R
[51] Int. Cl.² ..................................... C07D 301/20
[58] Field of Search ........................... 260/348.5 L

[56] References Cited

UNITED STATES PATENTS

| | | | |
|---|---|---|---|
| 3,434,975 | 3/1969 | Sheng et al. ...................... | 252/431 |
| 3,489,775 | 1/1970 | de Roch et al. ................... | 260/348.5 L |
| 3,502,740 | 3/1970 | Zajacek et al. .................... | 260/681 |
| 3,526,645 | 9/1970 | Vangermain et al. .............. | 260/348.5 L |
| 3,538,124 | 11/1970 | Sheng et al. ...................... | 260/348.5 L |
| 3,649,648 | 3/1972 | Fetterman ......................... | 260/348.5 L |

FOREIGN PATENTS OR APPLICATIONS

| | | |
|---|---|---|
| 641,452 | 12/1963 | Belgium |
| 807,186 | 2/1969 | Canada |
| 799,502 | 11/1968 | Canada |

*Primary Examiner*—Norma S. Milestone
*Attorney, Agent, or Firm*—Delbert E. McCaslin

[57] ABSTRACT

Method for the molybdenum-catalyzed epoxidation of less reactive olefins such as the alpha-olefins and alpha-substituted olefins with the less stable organic hydroperoxides to give good yields of the epoxide by employing a critical amount of a stabilizing agent consisting of a $C_3$ to $C_9$ secondary or tertiary monohydric alcohol.

6 Claims, No Drawings

EPOXIDATION OF OLEFINS WITH LESS STABLE ORGANIC HYDROPEROXIDES BY USING AN ALCOHOL STABILIZING AGENT

CROSS REFERENCE TO RELATED APPLICATION

This is a divisional of application Ser. No. 290,592 filed Sept. 20, 1972, now U.S. Pat. No. 3,862,961, which in turn is a continuation-in-part of application Ser. No. 95,375, filed Dec. 4, 1970 and now abandoned.

BACKGROUND OF THE INVENTION

This invention relates to a method for the epoxidation of olefins of lower reactivity, such as propylene with a less stable organic hydroperoxide, such as cyclohexyl hydroperoxide in the presence of a molybdenum-containing catalyst to give high hydroperoxide conversions and high yields of epoxide product, by employing a critical amount of a stabilizing agent consisting of a secondary or tertiary monohydric alcohol having from 3 to 9 carbon atoms such as tertiary butyl alcohol.

In recent years an olefin epoxidation process has been developed wherein the olefinic compound is epoxidized utilizing an organic hydroperoxide as the oxidizing agent and a molybdenum-containing catalyst. This process and the catalysts therefor have been widely described in both U.S. and foreign patents. The process and catalysts are described in U.S. Pat. 3,351,635 (1967) and Belgium Pat. No. 674,076, dated June 20, 1966. Additional molybdenum-catalysts for this reaction are described in U.S. Pat. Nos. 3,434,975 (1969); 3,453,218 (1969) and 3,480,563 (1969).

This process gives extremely good conversions and yields when a highly stable hydroperoxide is utilized to epoxidize a reactive olefin. Thus, commercially, tertiary butyl hydroperoxide is used as the oxidizing agent with excellent results. There is one disadvantage of limiting the oxidizing agent solely to tertiary butyl hydroperoxide and that arises since the reduction product is tertiary butyl alcohol and, accordingly, in order to render the process economically feasible, it is necessary to use or sell this by-product as well as the olefin epoxide product.

Various other hydroperoxides less stable than tertiary butyl hydroperoxide have been proposed since their corresponding reduction product, i.e. the alcohol, has potentially greater value as such or as an intermediate in the production of more valuable products. Unfortunately, heretofore, when attempts were made to use these less stable hydroperoxides, for example cyclohexyl hydroperoxide or amylene hydroperoxide, poor conversions and low yields were obtained, particularly when they were used to epoxidize less reactive olefins, such as the alpha-olefins (terminally unsaturated olefins) or olefins with electron withdrawing groups alpha to the double bond, i.e. chloro, hydroxyl and similar groups. An example of such less reactive olefins are the allyl chloro compounds.

It is only when these less stable hydroperoxides are used to epoxidize the highly reactive olefinic compounds such as the internal olefins, i.e. compounds having alkyl groups surrounding the double bond, that desired high conversions and yields are obtained. Thus, even though many of the derivatives from these hydroperoxides would have potentially a high value, they were not used commercially in the epoxidation of propylene to propylene oxide, one of the most useful epoxide compounds, since this compound is an alpha-olefin and thus is less reactive. When their use was attempted it was found that both the conversion of the hydroperoxide and yield of epoxide were poor.

The instant invention provides a method for obviating these difficulties and permits the use of the less stable hydroperoxide as the oxidizing agent in conjunction with a monlybdenum-containing catalyst to epoxidize even the less reactive olefins such as the alpha-olefins and the olefins substituted with an electron withdrawing group on the carbon alpha to the double bond to give excellent hydroperoxide conversion and high yields of the epoxide product. Important examples of such compounds are propylene and allyl chloride or allyl alcohol, respectively. This method employs a critical amount of a stabilizer compound which is a secondary or tertiary monohydric alcohol having from 3 to 9 carbon atoms.

SUMMARY OF THE INVENTION

In accordance with the present invention a $C_3$ to $C_{20}$ alpha-olefin or a $C_3$ to $C_{20}$ olefin having an electron-withdrawing substituent on the carbon alpha to the double bond is epoxidized using an organic hydroperoxide which is relatively unstable as the oxidizing agent in the presence of a molybdenum-containing catalyst and a stabilizer compound consisting of a secondary or tertiary monohydric alcohol having from 3 to 9 carbon atoms in the molecule which compound is present in amounts ranging from 1.5 moles to 3 moles per mole of the hydroperoxide oxidizing agent. The presence of the stabilizer compound permits the use of the less stable hydroperoxides in the epoxidation of the less reactive olefins with high conversion of the hydroperoxide and high yields of the epoxide.

It is an object of this invention, therefore, to provide a method for the epoxidation of olefins having from 3 to 20 carbon atoms and relatively difficult to epoxidize.

It is another object of this invention to provide a method for employing relatively less stable organic hydroperoxide as the oxidizing agent for the epoxidation of $C_3$ to $C_{20}$ olefins which are relatively difficult to epoxidize.

It is another object of this invention to provide a method for employing relatively less stable organic hydroperoxides as the oxidizing agent for the molybdenum catalyzed epoxidation of $C_3$ to $C_{20}$ olefins which are relatively difficult to epoxidize by employing as a stabilizing compound a secondary or tertiary monohydric alcohol as a stabilizing compound.

Other objects of this invention will be apparent from the following description of the preferred embodiments and from the claims.

DESCRIPTION OF THE PREFERRED EMBODIMENTS

The instant invention is applicable to the alpha-olefins having from 3 to 20 carbon atoms in the molecule, preferably straight chain although branched chain compounds can also be employed. Examples of these are propene, butene-1, pentene-1, hexene-1, heptene-1, octene-1 and the like ranging up to eicosene-1. It is also applicable to terminal olefins having an electron withdrawing substituent on the carbon alpha to the double bond. These olefinic compounds are characterized by the formula

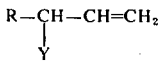

wherein R is hydrogen or an alkyl group having from 1 to 17 carbon atoms and Y is hydrogen or an electron withdrawing group such as a halogen, — OH, — CN or the like. These olefins are considerably more difficult to epoxidize then are the internal olefins or olefins wherein there is considerable substitution of alkyl groups, for example, on the carbons of the double bond.

The hydroperoxides which are employed in this invention are those which are commonly considered relatively unstable as compared to tertiary butyl hydroperoxide particularly when such hydroperoxides are in the presence of a molybdenum catalyst. Tertiary butyl hydroperoxide is a very stable compound considering the type of compound which it is, i.e. a peroxide, and is stable even in the presence of molybdenum catalysts. For this reason it has been employed as the oxidizing agent in epoxidation reactions wherein the aforementioned difficulty epoxidizable olefins are to be epoxidized since optinum conditions can be used with the result that excellent hydroperoxide conversions and yields are obtained. When hydroperoxides less stable than tertiary butyl hydroperoxide are employed the conversions are poor and the yields low. These less stable hydroperoxides to which this invention is directed are in particular cyclohexyl hydroperoxide and amylene hydroperoxide.

The alcohol and stabilizing agents which are employed in the method of the instant invention are the monohydric secondary and tertiary alcohols having from 3 to 9 carbon atoms in the molecule. Primary alcohols cannot be employed in the method of this invention since these attack the epoxide product thereby decreasing the yield of the epoxide because of side reactions and thus defeating the objects of this invention. Secondary and tertiary alcohols, however, are very much less reactive, with the tertiary being the least reactive with the epoxide.

Examples of secondary alcohols which can be employed are iso-propyl alcohol (2-propanol); 2-butanol; 2-pentanol; 3-pentanol; 4-methyl-2-pentanol; 2-methyl-3-pentanol; 2,4-dimethyl-3-pentanol; 2-hexanol; 5-methyl-2-hexanol; 3-hexanol; 5-methyl-3-hexanol; 2-heptanol; 3-heptanol; 4-heptanol; 2,6-dimethyl-4-heptanol; 2-octanol; 3-octanol; 4-octanol; 2-nonanol; 3-nonanol; 4-nonanol; 5-nonanol; cyclohexanol; the methyl cyclohexanols and the like.

Examples of the tertiary alcohols which can be employed are tertiary butyl alcohol (2-methyl-2-propanol); 2-methyl-2-pentanol; 2,4-dimethyl-2-pentanol; 3-methyl-3-pentanol; 2,3-dimethyl-3-pentanol; 3-ethyl-3-pentanol; 3-ethyl-2-methyl-3-pentanol; 2-methyl-2-hexanol; 3methyl-3hexanol; 3-ethyl-3-hexanol; 3-ethyl-5-methyl-3-hexanol; 2-methyl-2-heptanol; 3-methyl-3-heptanol; 4-methyl-4-heptanol; 4-ethyl-4-heptanol; 2-methyl-2-octanol; 2-phenyl-2-propanol and the like.

The tertiary alcohols are somewhat preferred over the secondary alcohols since they tend to attack the epoxides the least. Among the tertiary alcohols, tertiary butyl alcohol is the most preferred as the stabilizing agent of this invention.

The epoxidation reaction can be carried out using a mole ratio of olefin to hydroperoxide in the range of 1:1 to 30:1. Preferably an excess of olefin is employed to provide maximum opportunity for high hydroperoxide conversions, thus, the preferred range is from about 1.2:1 to 6:1. It should be noted that at the higher ratios the volume is too large to be commercially feasible, but the least stable hydroperoxides require the highest olefin to hydroperoxide ratios.

The epoxidation reaction is carried out at temperatures normally employed for the molybdenum-catalyzed reaction using an organic hydroperoxide, such as tertiary butyl hydroperoxide, as the oxidizing agent. A broad range of from 50° C. to 140° C. can be used with a more preferable range being from 60° C. to 100° C. The most preferred range for this reaction is from about 70° C. to 90° C. The reaction can be carried out at atmospheric pressure or in the case of epoxides which vaporize at the reaction temperature employed, reaction is carried out at the autogenous pressure of the reaction mixture at the particular temperature employed. Thus, the reaction is carried out in the liquid phase. The amount of alcohol stabilizer has been found to be critical and the mole ratio of the stabilizer to hydroperoxide must range from 1:1 to 3:1 and preferably from 1.5:1 to 2.5:1. It has been found that if this mole ratio of olefin to hydroperoxide is at the higher end of the range, then less stabilizer is required but it is preferred not to use the hight olefin to hydroperoxide ratios. The stabilizer is not a solvent and does not behave as a solvent. Thus, for example, solvents such as benzene which are known solvents for the reaction can be employed, but in the absence of the alcohol stabilizer of this invention no marked improvement in conversion or yield of epoxide can be obtained. Moreover, in general solvent effects do not depend upon quantities, i.e. molar ratios. In the instant invention it is necessary to utilize an amount of stabilizer within the ranges specified in order to obtain the improvements desired in accordance with the objects of this invention.

The molybdenum-containing catalysts which can be used in this process are any of the catalysts which have been disclosed in the process of epoxidizing olefinic compounds with an organic hydroperoxide. The molybdenum compounds which can be used include both inorganic and organic compounds of known structure and also those the exact structure of which is not known, for example, the reaction product of molybdenum metal with an organic hydroperoxide in the presence of a saturated $C_1$ - $C_4$ aliphatic alcohol as shown in the above-mentioned patent, U.S. Pat. No. 3,434,975. The various molybdenum compounds which have been disclosed as being useful include the oxides, for example molybdenum dioxide, molybdenum sesquioxide, molybdenum trioxide, molybdenum pentoxide, the chlorides, for example, molybdenum pentachloride, the coordinate complexes such as molybdenum hexacarbonyl, the acids and the corresponding salts wherein the molybdenum is contained in the anionic portion of the molecule, for example, and the molybdic acids and the corresponding molybdates.

In addition to these simple compounds the high molecular weight complex heteropoly acids and salts of molybdenum can be utilized. The heteropoly acids are complex inorganic compounds having a molecular weight ranging up to 3000 or higher and are comprised of a high molecular weight heteropoly anion containing 2 to 18 hexavalent metal atoms surrounding one or more hetero atoms. These complexes of molybdenum are known as the heteropolymolybdates and an example is sodium-silico-12-molybdate. The hetero atoms in the heteropoly anions are most commonly phosphorus or silica, although arsenic, germanium, tin, titanium, zinc and other elements also are known to function as hetero atoms in the heteropoly complexes.

In addition to the heteropoly compounds which are completely inorganic, the heteropoly acids and salts which are formed by reaction between simple salts and organic acids are also suitable. An example of these are the oxalomolybdates and the like. Other organo-molybdenum compounds may be employed, for example, molybdenyl (IV) acetylacetonate, $MoO_2$ $(C_5H_7O_2)_2$, molybdenum (III) acetylacetonate, $Mo(C_5H_7O_2)_3$, and similar organo-molybdenum compounds.

It has been found that any molybdenum compound is suitable as the catalyst in this reaction since it is the molybdenum which is critical and not the remainder of the compound. Those compounds which are soluble in the reaction medium are somewhat more preferred, although even those compounds considered insoluble, or which appear insoluble, produce the desired reaction.

In the examples which follow molybdenum hexacarbonyl and molybenyl (IV) acetylacetonate catalysts were employed since these compounds are readily available in the laboratory and are representative of the compounds which can be used but it is to be understood that any molybdenum compound is effective in the method of this invention in accordance with the prior art on this epoxidation process.

The amounts of molybdenum-containing catalyst which may be employed in the process of this invention are the ordinary catalytic amounts which are normally employed in the olefin epoxidation process using an organic hydroperoxide as the oxidizing agent. These can range from 20 parts per million (ppm) by weight of molybdenum based on the weight of the reaction mixture to 10,000 ppm by weight of molybdenum based on the weight of the reaction mixture. Generally from 50 ppm by weight to 1000 ppm by weight is used and since in the process of this invention the rate of reaction is slowed somewhat by the alcohol stabilizer it is preferred to use amounts of catalyst toward the higher end of the range.

The following examples are provided to illustrate the invention in additional detail and to show the various specific and preferred embodiments.

The conditions employed are set forth for example, however, it will be noted that in several examples the catalyst concentration is given in moles molybdenum per liter of reaction mixture. This was convenient for laboratory scale runs and of course the ppm by weight can be calculated from the known amounts of each component and its specific gravity. In general a concentration of 0.001 moles molybdenum per liter of reactant mixture represents approximately 125 ppm by weight of the weight of such mixture.

EXAMPLE I

Comparative runs were made using octene-1 and octene-2 as the olefins, cyclohexyl hydroperoxide as the oxidizing agent and molybdenum hexacarbonyl as the catalyst. The cyclohexyl hydroperoxide was a commercial sample which contained in weight per cent: cyclohexyl hydroperoxide-47; cyclohexanol-18; cyclohexanone-16; cyclohexane-19. The sample was dried over magnesium sulfate before use. The runs were carried out by heating a 5 ml. aliquot portion of a solution containing 10 g. of the hydroperoxide sample, 15 g. of the olefin and 0.02 g. of $Mo(CO)_6$ in a sealed tube at 90° C. for various times as shown in the Table I. This mixture was modified by adding various amounts of either an alcohol stabilizer or a solvent, but in each of such runs a 5 ml. aliquot portion was used as the reaction mixture. The variables as well as the conversions and yields are shown in the Table I. In this example and in all of the examples which follow conversion refers to weight per cent hydroperoxide converted based on the original weight of hydroperoxide and epoxide yield is in mole per cent, i.e. moles of epoxide produced per mole of hydroperoxide converted times 100. In all of the examples, also wherein a sealed tube was employed as the reactor it was sufficiently small such that substantially all of the reaction mixture was in the liquid phase.

TABLE I

| Run No. | Olefin | Stabilizer | Solvent | Time Min. | Conversion | Epoxide Yield |
|---|---|---|---|---|---|---|
| 1 | octene-1 | O | O | 30 | 65 | 59 |
| 2 | octene-1 | O | O | 60 | 88 | 58 |
| 3 | octene-2 | O | O | 30 | 100 | 91 |
| 4 | octene-2 | O | O | 60 | 100 | 91 |
| 5 | octene-1[(1)] | TBA[(2)] | O | 60 | 91 | 80 |
| 6 | octene-1[(1)] | TBA[(2)] | O | 90 | 95 | 75 |
| 7 | octene-1[(1)] | TBA[(3)] | O | 60 | 79 | 84 |
| 8 | octene-1[(1)] | TBA[(3)] | O | 90 | 91 | 83 |
| 9 | octene-1 | CH[(4)] | O | 30 | 91 | 75 |
| 10 | octene-1 | CH[(4)] | O | 60 | 96 | 71 |
| 11 | octene-1 | | B[(5)] | 30 | 55 | 54 |
| 12 | octene-1 | | B[(5)] | 60 | 87 | 59 |
| 13 | octene-1 | | O-1[(6)] | 30 | 64 | 65 |
| 14 | octene-1 | | O-1[(6)] | 60 | 90 | 67 |

[(1)]0.03 g. of $Mo(CO)_6$ used instead of 0.02 g.
[(2)]5.0 g. of tertiary butyl alcohol added to the basic reaction mixture.
[(3)]10.0 g. of tertiary butyl alcohol added to the basic reaction mixture.
[(4)]5.0 g. of cyclohexanol added to the basic reaction mixture.
[(5)]5.0 g. of benzene added to the basic reaction mixture.
[(6)]5.0 g. of ocetne-1 added to the basic reaction mixture.

These results show the slow conversions and yields obtained with octene-1 in the absence of an alcohol stabilizer, runs 1 and 2, but that octene-2 which is a far more reactive olefin gives excellent yields and conversions, runs 3 and 4. Runs 5, 6, 7 and 8 show that the addition of tertiary butyl alcohol greatly improves both conversion and yields with octene-1, and runs 9 and 10 show that a secondary alcohol also improves yields and conversions but not to the same extent as the tertiary alcohol. Runs 11 and 12 demonstrate that the best solvent normally used in epoxidation reactions does not improve conversions or yields thus showing that the use of the alcohol is not a solvent effect. Finally in runs 13 and 14 additional octene-1 is employed, but its sole effect is simply that of increasing the yield as would be expected by increasing the mole ratio of olefin to hydroperoxide, but no increase in hydroperoxide conversion is obtained.

EXAMPLE II

A large number of runs were carried out using amylene hydroperoxide as the oxidizing agent and propylene as the alphaolefin. Molybdenum hexacarbonyl was employed as the catalyst and the same sealed tube method was used as described in the preceding example including no addition of benzene and addition of benzene to constant volume. The amylene hydroperoxide consisted of a mixture of 3-methyl-3-hydroperoxo-1-butene and 2-methyl-3-hydroperoxo-1-butene. Various olefin to hydroperoxide mole ratios were employed as well as various temperatures and times. The catalyst concentrations were essentially the same as in Example I, i.e. slightly in excess of 0.001 moles per liter of liquid reactants.

It was found from this large number of runs that with benzene as the sole solvent and with no stabilizer present good conversions of hydroperoxide could be obtained but the yield of propylene oxide was very low. With tertiary butyl alcohol as the stabilizer in the critical range of amounts there was obtained good conversions of hydroperoxide and quantitative yields of propylene oxide. It was further found that in the absence of the stabilizer a mole ratio of olefin to hydroperoxide of 20:1 was required to obtain only good propylene oxide yields.

EXAMPLE III

Runs were made using the amylene hydroperoxide of Example II as the oxidizing agent, octene-1 as the olefin and molybdenyl (IV) acetylacetonate as the catalyst in sealed tubes. Temperatures ranging from about 70° C. to 90° C. were used with various mole ratios of olefin to hydroperoxide ranging from 10:1 to 30:1 and catalyst concentrations in the same range. The addition of tertiary butyl alcohol gave the usual improvement in yield whereas n-propyl alcohol and methanol failed to show the same improvements.

In general it has been found that cyclohexyl hydroperoxide and amylene hydroperoxide are less stable since these molecules contain no aromatic ring attached to the alkyl portion of the molecule having the hydroperoxide group. Thus cumene hydroperoxide and ethyl benzene hydroperoxide are both more stable than either cyclohexyl hydroperoxide (all methylene groups) or amylene hydroperoxide.

Reaction times which can be used depend upon the olefin being epoxidized, the hydroperoxide used, the alcohol used as the stabilizer, the temperature employed and the conversion and yield desired per pass. Hence generalizations are difficult to make but in most systems times ranging from about 15 minutes to 4 hours will give the desired results.

The reaction conditions in the examples given herein were not optimized as would be done if plant scale reactions were being investigated. The yield of the 1,2-epoxyalkane products obtained from the epoxidation of the alpha-olefins, such as 1,2-epoxyoctane and 1,2-epoxypropane (propylene oxide) as well as the other epoxides, i.e. the 2,3-epoxyoctane from octene-2 were determined both by an oxirane titration standard method and by gas chromatographic analysis. Good checks were found between the two methods.

Similar improved conversions and yields are obtained when olefins having an electron withdrawing group on the carbon alpha to the double bond, for example, allyl chloride or allyl alcohol are epoxidized by the method of this invention using an alcohol stabilizer.

As has been stated primary alcohols have not been found to be effective as stabilizers and in general they decrease the hydroperoxide conversion very seriously.

We claim:
1. A method for the epoxidation of olefins characterized by having the formula

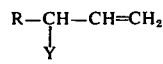

wherein R is hydrogen or an alkyl group having from 1 to 17 carbon atoms and Y is hydrogen, employing as the oxidizing agent a less stable organic hydroperoxide selected from the group consisting of cyclohexyl hydroperoxide and amylene hydroperoxide which comprises contacting said olefin with said hydroperoxide in the presence of a molybdenum-containing catalyst and as a stablilizing compound cyclohexanol at a temperature ranging between 50°C. to 140°C. under a pressure of at least the autogenous pressure of the reaction at the temperature employed, and with the mole ratio of said stabilizing compound to said hydroperoxide being in the range of from about 1:1 to 3:1.

2. A method according to claim 1 wherein said ratio of stabilizing compound to said hydroperoxide is in the range of from about 1.5:1 to 2.5:1.

3. The method according ot claim 1, wherein the olefin is propylene.

4. The method according to claim 1, wherein the olefin is ocetene-1.

5. The method according to claim 1, wherein the hydroperoxide is cyclohexyl hydroperoxide.

6. The method according to claim 1, wherein the hydroperoxide is amylene hydroperoxide.

* * * * *